United States Patent [19]

Wolfe et al.

[11] Patent Number: 5,162,507

[45] Date of Patent: Nov. 10, 1992

[54] PROCESS FOR RECOVERING PURIFIED, OXIDIZED, RENATURED RECOMBINANT INTERLEUKIN-2 FROM MICROORGANISMS

[75] Inventors: Sidney N. Wolfe, El Cerrito; Glenn J. Dorin, San Rafael; John T. Davis, Berkeley; Flint Smith, Gardon Grove; Amy Lim, Hercules; Robert Weissburg, Oakland, all of Calif.

[73] Assignee: Cetus Corporation, Emeryville, Calif.

[21] Appl. No.: 406,365

[22] Filed: Sep. 12, 1989

Related U.S. Application Data

[63] Continuation-in-part of Ser. No. 167,144, Mar. 25, 1988, abandoned, which is a continuation-in-part of Ser. No. 48,408, May 11, 1987, abandoned.

[51] Int. Cl.$^5$ ............................ C07K 3/00; C07K 3/12
[52] U.S. Cl. .................................. 530/412; 530/351; 530/416; 530/417; 530/418; 530/419
[58] Field of Search ................ 530/351, 412, 416–417, 530/418, 419

[56] References Cited

U.S. PATENT DOCUMENTS

| | | | |
|---|---|---|---|
| 4,476,049 | 10/1984 | Kung | 260/112 |
| 4,569,790 | 2/1986 | Koths | 260/112 |
| 4,656,255 | 4/1987 | Seely | 530/412 |
| 4,659,568 | 4/1987 | Heilman, Jr. | 424/88 |
| 4,677,196 | 6/1987 | Rausch et al. | 530/412 |
| 4,766,205 | 8/1988 | Ghosh-Dastidar | 530/402 |
| 4,766,224 | 8/1988 | Rausch | 530/412 |
| 4,801,691 | 1/1989 | Auer | 530/399 |
| 4,923,967 | 5/1990 | Bobbitt et al. | 530/351 |
| 4,931,543 | 6/1990 | Halenbeek et al. | 530/351 |

FOREIGN PATENT DOCUMENTS

| | | |
|---|---|---|
| 4307085 | 12/1985 | Australia . |
| 0092163 | 10/1983 | European Pat. Off. . |
| 0114506 | 8/1984 | European Pat. Off. . |
| 0147819 | 7/1985 | European Pat. Off. . |
| 0206828 | 12/1986 | European Pat. Off. . |
| 0213881 | 3/1987 | European Pat. Off. . |
| 61-257931 | 11/1986 | Japan . |
| 8808850 | 11/1988 | World Int. Prop. O. . |

OTHER PUBLICATIONS

Sofer et al., Biotechnology, vol. 2, pp. 1035–1038 (1986).
Mochizuki et al., J. Immunol. Meth. vol. 39 pp. 185–201 (1980).
Tsuji et al., Biochem., vol. 26, No. 11, pp. 3129–3134 (1987).
Browning et al., Anal. Biochem., vol. 155(1), pp. 123–128 (1986) (Abstract).
Welte et al., J. Exp. Med., vol. 156, pp. 454–464 (1982).
Weber et al., 1971, J. of Biological Chemistry, 246:4504–4509.
Light, 1985, Bio/Techniques, 3:289–397.

Primary Examiner—F. T. Moezie
Assistant Examiner—Andrew G. Rozycki
Attorney, Agent, or Firm—Philip L. McGarrigle; Lisabeth F. Murphy

[57] ABSTRACT

A process for recovering highly pure, recombinant IL-2 from transformed microorganisms in which the cells are disrupted; impure recombinant IL-2 is isolated in the form of refractile bodies from the disruptate; the impure IL-2 is dissolved and denatured with at least 6M guanidine hydrochloride containing a reducing agent; the reduced IL-2 is precipitated and resolubilized; the reduced solubilized IL-2 therein is oxidized by a controlled oxidation; the oxidized IL-2 is refolded by reducing the concentration of guanidine hydrochloride in the solution; and the oxidized, refolded IL-2 is further purified by ion exchange chromatography or hydrophobic interaction chromatography and ion exchange chromatography.

38 Claims, 2 Drawing Sheets

FIG. 2

PROCESS FOR RECOVERING PURIFIED, OXIDIZED, RENATURED RECOMBINANT INTERLEUKIN-2 FROM MICROORGANISMS

CROSS REFERENCE TO RELATED APPLICATION

This application is a continuation-in-part of copending application U.S. Ser. No. 167,144, filed Mar. 25, 1988, now abandoned which is continuation-in-part of copending application U.S. Ser. No. 048,408, filed May 11, 1987 now abandoned. Both applications are hereby incorporated by reference in their entireties.

DESCRIPTION

TECHNICAL FIELD

The invention is in the field of biochemistry and relates to a process for recovering purified, renatured recombinant interleukin-2(IL-2) from the microorganisms in which it is produced.

BACKGROUND

IL-2, a lymphokine which is produced by normal peripheral blood lymphocytes and induces proliferation of antigen or mitogen stimulated T cells after exposure to plant lectins, antigens, or other stimuli, was first described by Morgan et al., 1976, Science 193:1007-1008. Then called T cell growth factor because of its ability to induce proliferation of stimulated T lymphocytes, it is now recognized that in addition to its growth factor properties it modulates a variety of functions of immune system cells in vitro and in vivo and has been renamed IL-2. IL-2 is one of several lymphocyte-produced messenger-regulatory molecules that mediate immunocyte interactions and functions.

IL-2 was initially made by cultivating human peripheral blood lymphocytes (PBL) or other IL-2-producing cell lines. See, for instance, U.S. Pat. No. 4,401,756. Recombinant DNA technology has provided an alternative to PBLs and cell lines for producing IL-2. Taniguchi et al., 1983, Nature 302:305-310; U.S. Pat. No. 4,738,927, issued Apr. 19, 1988; and Devos, 1983, Nucleic Acids Research 11:4307-4323 have reported cloning the human IL-2 gene and expressing it in microorganisms.

Native human IL-2 is an antigen-nonspecific, genetically unrestricted soluble factor produced by erythrocyte rosette positive T cells stimulated with antigens, mitogens or alloantigens. It is a protein with a reported molecular weight in the approximate range of 13,000 to 17,000 daltons (S. Gillis and J. Watson, 1980, J Exp Med 159:1709) and an isoelectric point in the approximate range of pH 6-8.5.

Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines.

Human IL-2 has been obtained from genetically engineered E. coli as an unglycosylated protein with biological activities equivalent to those of native, glycosylated IL-2. (Taniguchi et al., 1983, Nature 11:4307-4323; Rosenberg et al., 1984, Science 223:1412-1415; Wang et al., 1984, Science 224:1431-1433; and Doyle et al., 1985, J Biol Resp Modifiers 4:96-109). Rosenberg and his coworkers have shown that systemic administration of recombinant IL-2 in high doses causes regression of established metastatic cancers in mice (Rosenberg et al., 1985, J Exp Med 161:1169-1188); and, in conjunction with lymphokine-activated killer cells (Rosenberg et al., 1985, New Eng J Med 313:1485-1492) and tumor-infiltrating lymphocytes (Rosenberg et al., 1986, Science 233:1318-1321), in humans.

U.S. Pat. No. 4,518,584 discloses muteins (analogs) of IL-2 in which the cysteine normally occurring at position 125 of the wild-type or native molecule has been replaced with a neutral amino acid, such as serine or alanine. European Patent (EP) publication 200,280 discloses muteins of IL-2 whereby the methionine at position 104 has been replaced by a conservative amino acid.

Microbially produced IL-2 is not glycosylated and is primarily produced in a denatured state. It is largely insoluble and, when expressed at high levels, it precipitates intracellularly in the form of "refractile" or "inclusion" bodies which appear as bright spots visible within the cell under a phase contrast microscope at magnifications down to 1000-fold. The problem addressed by the present invention is how to efficiently recover the IL-2 from the cell in a purified, cystine-bridged, renatured form that is acceptable for clinical use.

The heretofore available methods for recovering microbially produced IL-2 are described below.

U.S. Pat. No. 4,569,790 describes a process for recovering recombinant IL-2 from an IL-2-producing microorganism in which the cell is disrupted, the disruptate is extracted with an aqueous solution of a chaotropic agent such as urea, the IL-2 is solubilized with a surfactant, e.g., sodium dodecyl sulfate (SDS), and the IL-2 is separated in the presence of a reducing agent.

Commonly owned U.S. Pat. Nos. 4,530,787 and 4,572,978 described processes for purifying recombinant IL-2 from microorganisms in which partially purified reduced IL-2 is selectively oxidized under controlled conditions to its oxidized (cystine) form. The former patent uses o-iodosobenzoic acid as an oxidizing agent and the latter uses $Cu+2$ cation as an oxidation promoter.

European Patent publication 206,828 published 30 Dec. 1986, and entitled "Process for Recovering Refractile Bodies Containing Heterologous Proteins from Microbial Hosts" discloses methods for recovering and purifying refractile bodies of IL-2 from E. coli. To isolate the refractile material, the processes initially involve disrupting the cell wall and membrane of the host cell, removing greater than 99% by weight of the salts from the disruptate, redisrupting the desalted disruptate, adding a material to the disruptate to create a density or viscosity gradient in the liquid within the disruptate, and separating the refractile material from the cellular debris by high-speed centrifugation. The IL-2 is then solubilized with a solubilizing agent such as SDS, chromatographed to remove high molecular weight contaminants, oxidized, and purified by a combination of HPLC, ultrafiltration and gel filtration.

An abstract titled "Purification and Renaturation of Recombinant Interleukin-2" presented at the 6th International Symposium on HPLC of Proteins, Peptides and Polynucleotides at Baden-Baden, West Germany in October 1986 describes a process in which recombinant IL-2 is solubilized from inclusion bodies with 6M guanidine hydrochloride/10 mM dithiothreitol (DTT) and purified in a reduced, denatured form by FPLC gel permeation. The solution from the FPLC gel permeation is diluted to effect renaturation and autoxidation. In this regard U.S. Pat. Nos. 4,511,502, 4,511,503, 4,512,922, and 4,518,526, and EP publication 114,506 describes a similar procedure for purifying heterologous proteins in general from refractile bodies. In such processes, the oxidation and renaturation of the IL-2 are carried out in a single step. However, because of disparate solubility characteristics between the reduced and oxidized forms of IL-2, it is difficult to achieve high yields of renatured oxidized IL-2 in such a process.

EP publication 145,390 describes a process for recovering rIL-2 from *E. coli* in which the cells are suspended in 7M guanidine hydrochloride, solids are removed by centrifugation, the rIL-2-containing supernatant is dialyzed to remove the guanidine hydrochloride and the dialyzate is purified by anion exchange chromatography, gel filtration and RP-HPLC.

The present invention is directed to an improved recombinant IL-2 purification process in which the oxidation and renaturation are carried out in distinct steps.

DISCLOSURE OF THE INVENTION

The present invention relates to a high yield process in which IL-2 is separated from a cellular disruptate in the form of a refractile body, dissolved with a chaotropic agent and oxidized and renatured in separate steps followed by purification to a clinically acceptable level. More specifically, the present invention is a process for purifying recombinant interleukin-2 (IL-2) from a transformed microorganism containing the IL-2, comprising: isolating water insoluble IL-2 containing material; dissolving the water insoluble IL-2 containing material in a sufficient amount of a guanidine salt and a reducing agent; reducing the concentration of the guanidine salt, so that the IL-2 precipitates but the soluble proteins from the transformed microorganism remain soluble and are removed; whereby the IL-2 is substantially purified. Preferably steps (b) and (c) are repeated or the IL-2 containing precipitate is washed in acetate or a guanidine solution having a concentration between 2 and 4M. After reprecipitation or washing, the IL-2 is redissolved in guanidine or SDS and oxidized. If the IL-2 is dissolved in SDS, then the process purifying the IL-2 by reverse phase HPLC (RP-HPLC); dissolving the IL-2 in guanidine and removing the SDS; lowering the guanidine concentration to below 0.5M by diafiltration; and purifying the IL-2 by CM Sepharose chromatography. If the IL-2 is redissolved in guanidine, then the process further comprises either of the following options: (1) lowering the guanidine concentration to below 0.5M by diafiltration and purifying the IL-2 by CM Sepharose chromatography; or (2) lowering the guanidine concentration to below 0.5M by diafiltration; purifying the IL-2 by RP-HPLC; dialyzing the resulting IL-2 solution; and purifying the IL-2 by CM Sepharose chromatography.

Among other factors, the present invention is advantageous because it removes a substantial concentration of soluble contaminant proteins (that derive from the microorganism) in the first precipitation step. For example, the IL-2 is insoluble in water and needs to be solubilized in guanidine. When the IL-2 is precipitated by reducing the guanidine concentration, the water-soluble proteins from the microorganism are left in the solution (to be discarded). Thereafter, the IL-2 pellet is redissolved, purified and processed so that when the guanidine concentration is lowered at a later stage, the water-insoluble proteins from the microorganism are precipitated without precipitating the IL-2. Another advantage is in the reprecipation step. When the first IL-2 precipitate is redissolved and reprecipitated, more contaminant proteins are removed.

MODES FOR CARRYING OUT THE INVENTION

A. Definitions

As used herein, the term "IL-2" refers to recombinant interleukin-2 or interleukin-2-like polypeptides produced by a transformed microorganism and the amino acid sequence of which are the same as or similar or substantially homologous to the unglycosylated and/or glycosylated native interleukin-2. Examples of such recombinant IL-2s are those described in U.S. Pat. No. 4,738,927 and European published patent applications 91,539, 88,195, and 109,748, as well as those described in U.S. Pat. No. 4,518,584, copending, commonly assigned U.S. Ser. No. 893,186, filed Aug. 5, 1986, EP publication 200,280, and bovine IL-2 as described by Cerretti et al., 1986, *Proc Natl Acad Sci USA* 83:3223-3227. The disclosures of all these references are incorporated herein by reference.

The recombinant IL-2s particularly preferred herein are those biologically active muteins (analogs) of human IL-2 in which amino acid residues not essential to biological activity have been deliberately deleted in some instances or replaced with a conservative amino acid, as indicated below. More specifically, preferred recombinant IL-2s include those wherein the cysteine residue at position 125 is replaced with another amino acid, preferably neutral or conservative, to eliminate sites for intermolecular crosslinking or incorrect intramolecular disulfide and, optionally, the N-terminal alanine residue of the native counterpart is eliminated. As used herein, such neutral or conservative amino acids are glycine, serine, valine, alanine, leucine, iso leucine, tyrosine and methionine. More particularly, preferred recombinant IL-2 muteins in the formulations of this invention are those wherein (1) the cysteine residue at amino acid position 125 of the native counterpart is replaced by a serine residue (designated IL-2$_{ser}$125) or alanine residue (designated IL-2$_{ala}$125); or (2) the initial alanine residue is eliminated and the cysteine at position 125 is replaced by serine (designated des-alanyl-IL-2$_{ser}$125).

Other IL-2s particularly preferred herein are those biologically active muteins described in European Patent Publication 200,280 wherein oxidation-susceptible methionine residues are replaced with a neutral or conservative amino acid; a preferred mutein includes replacing the methionine at position 104 with a conservative amino acid such as alanine.

EP 200,280 also describes amino-terminal deletions of IL-2 wherein one or more of the first six amino acids are deleted. Preferred oxidation-resistant muteins include ala$_{104}$ser$_{125}$IL-2, ala$_{104}$IL-2, ala$_{104}$ala$_{125}$IL-2, val$_{104}$ser$_{125}$IL-2, val$_{104}$IL-2, val$_{104}$ala$_{125}$IL-2, des-ala$_1$ala$_{104}$ser$_{125}$IL-2, des- ala$_1$ala$_{104}$IL 2, des-ala$_1$ala$_{104}$ala$_{125}$IL-2, des-ala$_1$val$_{104}$ser$_{125}$IL-2, des-ala$_1$val$_{104}$IL-2, des- ala$_1$val$_{104}$ala$_{125}$IL-2, des-ala$_1$des pro$_2$ala$_{104}$ser$_{125}$IL-2, des-ala$_1$-des-pro$_2$ala$_{104}$IL-2, des-ala$_1$des-pro$_2$ala$_{104}$ala$_{125}$IL-2, des-ala$_1$des pro$_2$val$_{104}$ser$_{125}$IL-2, des-ala$_1$des-pro$_2$ val$_{104}$IL-2, des-ala$_1$des-pro$_2$val$_{104}$ala$_{125}$IL-2, des-ala$_1$des-pro$_2$des-thr$_3$ala$_{104}$ser$_{125}$IL-2, des-ala$_1$des-pro$_2$des-thr$_3$ala$_{104}$IL-2, des-ala$_1$des-pro$_2$-des thr$_3$ala$_{104}$ala$_{125}$IL-2, des-ala$_1$des-pro$_2$des thr$_3$-val$_{104}$ser$_{125}$IL-2, des-ala$_1$des-pro$_2$des-thr$_3$val$_{104}$IL-2, des-ala$_1$des-pro$_2$des-thr$_3$val$_{104}$ala$_{125}$IL-2, des ala$_1$des-pro$_2$des-thr$_3$des-ser$_4$ala$_{104}$ser$_{125}$IL-2, des-ala$_1$des pro$_2$des- thr$_3$des-ser$_4$ala$_{104}$IL-2, des-ala$_1$des pro$_2$des-thr$_3$des- ser$_4$ala$_{104}$ala$_{125}$IL-2, des-ala$_1$des-pro$_2$des-thr$_3$des-ser$_4$val$_{104}$ser$_{125}$IL-2, des-ala$_1$des-pro$_2$des thr$_3$des- ser$_4$val$_{104}$IL-2, des-ala$_1$des-pro$_2$des thr$_3$des- ser$_4$val$_{104}$ala$_{125}$IL-2, des-ala$_1$des-pro$_2$des-thr$_3$des- ser$_4$des ser$_5$ala$_{104}$ser$_{125}$IL-2, des-ala$_1$des-pro$_2$des-thr$_3$des-ser$_4$des-ser$_5$ala$_{104}$IL-2, des-ala$_1$des pro$_2$des-thr$_3$des ser$_4$des-ser$_5$ala$_{104}$ala$_{125}$-IL-2, des-ala$_1$des-pro$_2$des thr$_3$des-ser$_4$des-ser$_5$val$_{104}$-ser$_{125}$IL-2, des-ala$_1$des pro$_2$des-thr$_3$des-ser$_4$des-ser$_5$-val$_{104}$IL-2, des-ala$_1$des pro$_2$des-thr$_3$des-ser$_4$des-ser$_5$-val$_{104}$-ala$_{125}$IL-2, des-ala$_1$des-pro$_2$des-thr$_3$des-ser$_4$-des-ser$_5$des-ser$_6$ala$_{104}$ala$_{125}$IL-2, des-ala$_1$des-pro$_2$-des thr$_3$des-ser$_4$des-ser$_5$des-ser$_6$ala$_{104}$IL-2, des-ala$_1$des-pro$_2$des-thr$_3$des-ser$_4$des-ser$_5$des ser$_6$ala$_{104}$ser$_{125}$IL-2, des- ala$_1$des-pro$_2$des thr$_3$des-ser$_4$des-ser$_5$-des-ser$_6$val$_{104}$ser$_{125}$IL-2, des-ala$_1$des-pro$_2$des thr$_3$-des- ser$_4$des-ser$_5$des-ser$_6$val$_{104}$IL-2, or des-ala$_1$des-pro$_2$des- thr$_3$des ser$_4$des-ser$_5$des-ser$_6$val$_{104}$-ala$_{125}$IL-2.

Other amino-terminal deletions of IL-2 are disclosed in *Chemical Abstracts*(1987) 106:(21):170236f, an abstract of Japanese Patent Publication No. 61/225199, published 6, Oct. 1986, wherein any one of the first 15 amino acids of IL-2 are deleted. PCT 87/04714, published 13 Aug. 1987 describes deletions or replacements of one or more of the amino acid residues in positions 2 to 11 and/or 128 to 133 from the amino-terminal alanine of IL-2.

The precise chemical structure of the IL-2 protein will depend on a number of factors. As ionizable amino and carboxyl groups are present in the molecule, a particular recombinant IL-2 protein may be obtained as an acidic or basic salt, or in neutral form. All such preparations which retain their activity when placed in suitable environmental conditions are included in the definition of IL-2 proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IL-2 protein herein so long as the activity of the protein, as defined above, is not destroyed. It is expected, of course, that such modifications may quantitatively or qualitatively affect biological activity, either by enhancing or diminishing the activity of the protein in the various assays.

As used herein the term "transformed" in describing host microorganism cell cultures denotes a microorganism that has been genetically engineered to produce an IL-2 polypeptide that is capable of possessing the activity of native IL-2. Bacteria are preferred microorganisms for producing the IL-2 protein. *E. coli* is particularly preferred.

The term "chaotropic agent" refers to a compound or compounds which, in aqueous solution and in a suitable concentration, are capable of denaturing recombinatnt IL-2. Correlatively the term "strongly denaturing concentration" refers to a solution of a chaotropic agent which will effectively "unfold" or denature recombinant IL-2. Guanidine salts (e.g., the hydrochloride) and alkali metal thiocyanate (e.g., sodium thiocyanate) at concentrations in the range of about 4 to 9M, preferably 6-9M, are examples of chaotropic agent solutions that will dissolve and denature recombinant IL-2. Also, sodium dodecyl sulfate (SDS) at a concentration between 0.1% and 10% can be used.

Cell Growth

The IL-2-producing transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp. 80–85 (1980). In expression vectors involving the trp promoter, the tryptophan concentration in the medium is carefully controlled to become limiting at the time protein expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods.

Cell Disruption

Following concentration of the harvested culture, the cell membranes and cell walls of the microorganisms are disrupted. Preferably a compound which is non-toxic to humans, such as 1-octanol, in an amount of about 1% by weight of total components, is added to the disrupted cells to ensure that no viable recombinant organisms remain. Conventional cell disruption techniques such as homogenization, sonication, or pressure cycling may be used in this step of the process. The end point of the disruption step can be determined by monitoring the optical density with the absorbance at 260 nm of the suspension typically increasing with cell lysis and by microscopic observation. In any event, the disruption should break substantially all of the cells so that substantially no intact cells are carried through to subsequent steps.

Treatment of Disruptate to Isolate Insoluble IL-2 Bodies

After the cells have been disrupted, deionized water is preferably added to the disruptate and greater than 99% by weight of the salts are removed therefrom. The salts are water-soluble materials composed of oppositely charged small molecular weight ions. The removal of these salts to reduce the ionic strength of the disruptate may be accomplished by diafiltration using deionized water to flush out the ions or by centrifuging to pellet the cellular debris and refractile bodies followed by resuspension in deionized water. If diafiltration is employed, preferably deionized water is continuously added such that the rate of addition of water equals the filtration rate.

After the salts are essentially removed, optionally a compound such as 1-octanol may be added to the desalted disruptate, if not added earlier, to ensure that no viable recombinant organisms remain before containment is broken. The desalted disruptate is again disrupted as described above for the initial disruption.

After redisruption, density or viscosity is increased and/or a gradient is created during centrifugation in the liquid within the disruptate by adding a material to the disruptate. There are several means to accomplish this purpose, all relying on the sedimentation characteristics of the particles by varying the density and/or viscosity of the liquid phase. One means to accomplish this goal is to add a material which increases the density of the liquid to a p=rho of about 1.1 to 1.3 g/ml, preferably 1.13 to 1.17 g/ml.

Materials which may be used to accomplish this density increase include a sugar or mixture of sugars, such as, e.g., sucrose, dextrose, fructose, maltose, maltotriose, and other mono-, dior polysaccharides. Most preferably the sugar is sucrose. Alternatively, a two-phase system of materials such as, e.g., a glycerol/sucrose mixture may be used wherein the disrupted particles partition to the interface between the heavy and light phases and can be eluted by a liquid/liquid separation.

In addition, the viscosity of the liquid phase may be increased to from 5 to 10 cps by any suitable means such as by adding a viscous compound such as, e.g., sucrose or glycerol thereto. Also, a gradient is created if, e.g., the particles are in a 60% aqueous glycerol suspension while the centrifuge bowl contains 80% aqueous glycerol.

The IL-2-containing refractile bodies are separated from the cellular debris by high-speed centrifugation. By "high-speed centrifugation" is meant spinning the suspension in a centrifuge at about 8,000 to 40,000 times gravity (g), preferably about 10,000–20,000×g, for a suitable time period depending on the volume, generally about 10 minutes to seventy-two hours.

The particle pellet or paste resulting from the centrifugation contains approximately 15–70% by weight IL-2 as determined by SDS-polyacrylamide gel electrophoresis and by Lowry assay (Lowry et al., 1951, *J Biol Chem* 193: 265–275). This paste is diluted 1:1 with water and then dissolved and denatured by mixing with a solution of a strongly denaturing concentration of the chaotropic agent (preferably guanidine) and a reducing agent. This forms a slurry. The chaotropic agent and reducing agent are in an aqueous buffer at pH 7 to 9, preferably phosphate buffered saline or Tris buffer. pH adjustment may be accomplished by the addition of base such as NaOH. The w/v ratio of slurry to chaotrope/reducing agent will normally be in the range of 0.01:1 to 0.33:1 preferably 0.1 to 0.3:1. Reducing agents that can be employed during the dissolving/denaturing step include: $\beta$-mercaptoethanol, glutathione, cysteine and dithiothreitol (DTT). DTT is the preferred reducing agent. The concentration of the reducing agent in the medium will usually range between about 10 to 100 mM with approximately between 15 and 25 mM being the preferred concentration. Chelating agents such as ethylene diaminetetraacetic acid (EDTA) in concentrations of 1 to 50 mM, preferably between 1 and 10 mM, and buffers such as Tris.HCl at concentrations of 25 to 250 mM, preferably 50 mM, may be included in the solution. Elevated temperatures in the range of 25° C. to 50° C., preferably about 30° C., and a nitrogen blanket may be used in this step. The dissolution/denaturation will typically be complete after about 5 to 30 min of mixing. After this time, the mixture may be centrifuged, preferably at 2000×g to 10000×g for about 10 to 30 min, or filtered, to remove any undissolved materials. Afterwards, the denatured IL-2 is subjected to a controlled oxidation, however it is preferred to first subject the IL-2 to a purification by precipitation.

The reducing agent, along with other contaminating material, is removed using gel filtration, diafiltration, or precipitation. Gels that are capable of removing the reducing agent from the protein solution are commercially available. For instance, when DTT is used as a reducing agent Sephadex G-10, G-25, and G-50 gels may be used. The gel filtration will be run in a solution of the chaotropic agent that maintains the protein in solution. When guanidine hydrochloride is used, concentrations above about 6M are required to keep the IL-2 in solution and avoid precipitate formation. After removing the reducing agent the protein solution is diluted, if necessary, with the solution of chaotropic agent to a protein concentration of about 0.1 to 2 mg/ml, preferably about 0.25 to 1.0 mg/ml.

A preferred method of removing the reducing agent along with contaminating material employs precipitation techniques. The reduced IL-2 is diluted to approximately 1–5M guanidine, preferably 3.5M guanidine, and allowed to stand until the precipitation is complete, generally two to ten minutes. The IL-2 can be pelleted by centrifugation. Residual DTT may be removed by washing the pellet with a buffer, preferably using a 2–4M guanidine-containing buffer or a 1–2% polysorbate-80 containing buffer.

After the IL-2 has been precipitated, the pellet can be treated to remove more impurities. For example, the pellet can be washed (with 3.5M guanidine or sodium acetate) or reprecipitated using the procedure above (i.e. dissolve in 7M guanidine, but without DTT, then reduce the guanidine concentration to approximately 3.5M). Reprecipitation is preferred because soluble impurities that are partially coprecipitated with IL-2 may be removed upon reprecipitation.

After the IL-2 has been precipitated, it is redissolved in a chaotrope (such as guanidine or SDS) and oxidized. Preferred selective oxidation procedures are described in commonly owned U.S. Pat. Nos. 4,572,798 (using an oxidation promoter containing a $Cu^{+2}$ cation such as from $CuCl_2$, $Cu(NO_3)_2$, etc) and 4,530,787 (using o-iodosobenzoic acid), the disclosures of which are incorporated herein by reference. The $Cu^{+2}$ oxidation comprises reacting the aqueous solution of denatured IL-2 at a pH between about 5.5 and 9, preferably 6 to 8, and most preferably about 7.5, in the presence of air with at least an effective amount of an oxidation promoter containing a $Cu^{+2}$ cation. Controlled oxidation causes the formation of disulfide bridging in the IL-2 which conforms to the bridging in native IL-2 with no or minimal overoxidation and formation of nonconforming bridging or oligomers. Such oxidation enables the production of high yields of the recombinant IL-2 with the proper disulfide bridging.

The amount of oxidant or oxidation promoter employed is at least an effective amount for oxidation, i.e., an amount which at minimum will be necessary to conduct the oxidation reaction effectively within a convenient period of time. An effective amount is the amount approximately equivalent to the concentration of free sulfhydryl groups in the IL-2 which are destined to be involved in forming the desired disulfide bonds. Preferably, the amount of $CuCl_2$ will range from about 5 to 275 micromolar. In the case of o-iodosobenzoic acid the mole ratio of oxidant to IL-2 will preferably be in the range of about 0.05:1 to about 5:1, most preferably about 0.8:1 to about 1:2. The concentration of IL-2 in the reaction mixture is kept low, i.e., generally less than about 5 mg/ml, preferably about 0.05 to about 2 mg/ml, and more preferably about 0.1 to about 1 mg/ml, to reduce the likelihood of oligomer formation. The pH is maintained between 5.5 and 9, preferably between 7 and 8 in the o-iodosobenzoic acid oxidation.

The reduced IL-2 must remain in solution for effective oxidation to occur. Therefore, the reaction mixture must contain a sufficient concentration of chaotropic agent to keep the reduced IL-2 in solution. As indicated above, when guanidine hydrochloride is used, its concentration must be above 6M. At such concentrations, the IL-2 will be in a denatured form. For this reason, it is difficult in the case of IL-2 to carry out the oxidation and renaturation simultaneously and obtain high yields of renatured IL-2. SDS can also be used (as the guanidine hydrochloride may damage the stainless steel HPLC equipment). Preferably, the SDS concentration is between 0.1% and 2% in a phosphate buffer (see U.S. Pat. Nos. 4,572,798 and 4,530,787 referred to above).

The temperature used in the oxidation will normally be between about 20° C. and 40° C., conveniently room temperature. For $Cu^{+2}$ oxidation, increasing the reaction temperature increases the rate of reaction. The oxidation reaction may be effectively terminated by, e.g., lowering the pH to a level at which the reaction ceases, freezing the solution, or adding chelators such as EDTA to the reaction mixture. Oxidation time will normally be in the range of 5 minutes to 4 hours.

When the oxidation is complete, the concentration of the chaotropic agent (if it is guanidine hydrochloride) is reduced using dilution, dialysis, or diafiltration, to a level which permits the oxidized IL-2 to renaturate and refold into the configuration of native IL-2. Phosphate buffer or citrate buffer, 10 to 100 mM, preferably about 10 mM; NaCl, 10-150 mM, preferably 40 mM; and sucrose, 1-5%, preferably 2.5%, are preferred diluents. Preferably, the IL-2 is concentrated using an ultrafiltration membrane to avoid handling large volumes of solution. The concentration of guanidine hydrochloride agent is normally diluted or diafiltered to below about 2M, preferably below about 0.05M. The dilution will typically be carried out at about 4° C. to 25° C. At such temperatures and reduced guanidine hydrochloride concentration a precipitate of extraneous host protein forms. This precipitate is removed by filtration or centrifuging to provide a supernatant containing the oxidized, renaturated IL-2.

The renatured, oxidized IL-2 is then purified to remove endotoxins to a level that meets clinical specifications (i.e., less than about 0.1 ng endotoxin per ml of IL-2). The IL-2 is also preferably purified to remove pyrogen so as to be substantially free of pyrogens as measured by the U.S.P. rabbit pyrogen test at a dosage of $1.0 \times 10^3$ units/kg, preferably $3.3 \times 10^5$ units/kg). The purification may be achieved by ion exchange chromatography, or a combination of hydrophobic interaction and ion exchange chromatography, or by RP-HPLC.

The IL-2 may subsequently be loaded onto an ion exchange column such as a carboxymethyl agarose column (e.g., Pharmacia Fast-Flow Sepharose CM) that binds IL-2 at a pH of 6 to 7.5. The bound IL-2 may be eluted with an increasing salt gradient. The desired IL-2 elutes at approximately 150 mM salt with the lower isoelectric point forms of the protein eluting at lower salt concentrations.

In the hydrophobic interaction/ion exchange chromatography technique, $(NH_4)_2SO_4$ is added to the IL-2 solution to a concentration of at least about 1.0M, preferably about 1.25M. The solution is then loaded onto a hydrophobic interaction column, such as a phenyl agarose column (e.g., Pharmacia Phenyl Fast-Flow Sepharose column). Bound IL-2 is recovered from the column with a decreasing $(NH_4)_2SO_4$ gradient, with the IL-2 being collected in the fractions eluting at about 0.95 to 0.75M $(NH_4)_2SO_4$. Species of IL-2 and other impurities (bacterial host proteins) having lower isoelectric points than native IL-2 are then removed by cation exchange chromatography using an exchanger that binds IL-2 at a pH of 6 to 7.5. A carboxymethyl agarose column (e.g., Pharmacia Fast-Flow Sepharose CM) is a preferred preparative cation exchanger. The solution is contacted with the exchanger at the indicated pH range and the IL-2 is eluted from the exchanger using an ionic gradient. The desired IL-2 elutes at approximately 0.15M salt with the lower isoelectric point forms of the protein eluting at lower salt concentrations.

The HPLC purification of the IL-2 that has been oxidized in guanidine hydrochloride or SDS may be carried out in essentially the same manner as described in U.S. Pat. No. 4,569,790 followed by redissolution in a chaotropic agent and dialysis. Briefly, the solution of IL-2 is chromatographed, precipitated, and the resulting precipitate is taken up in the chaotropic agent solution. The chaotropic agent is then removed by dialysis or diafiltration. The IL-2 may be further purified by cation exchange chromatography.

An alternative purification scheme can be used in which the order of steps is adjusted to remove IL-2 having oxidized methionine residues while retaining a high yield and purity. For example, after the IL-2 is oxidized in the 7M guanidine, it is diafiltered and then purified using a RP-HPLC. After RP-HPLC purification, the resulting solution is dialyzed to remove the HPLC solvents and then purified on a carboxymethyl agarose column (e.g., Pharmacia Fast-Flow Sepharose CM). Preferably, the diafiltration is performed stepwise from about 7M to 1M guanidine, then from about 1M to 0.5M guanidine, then from about 0.5 to 0M guanidine. Also, it is preferred to add either glycine or arginine during the diafiltration to prevent IL-2 aggregation. It is further preferred to stepwise dialyze out the HPLC solvents then the acetic acid.

The purity of the renatured, oxidized IL-2 after the chromatography steps is at least about 95% and usually at least about 98%, as determined by reducing sodium dodecyl sulfate polyacrylamide gel electrophoresis (SDS-PAGE) analysis. This pure IL-2 has a solubility in PBS of at least about 5 mg/ml, a specific activity of at least about $1 \times 10^7$ units/mg, usually $5 \times 10^6$ to $2 \times 10^7$ units/mg as determined by the HT-2 cell proliferation assay, and endotoxin content of less than about 0.1 ng/mg of IL-2. Also, preferably the IL-2 is substantially free of pyrogens as determined by the U.S.P. rabbit pyrogen test at a dosage of $1.0 \times 10^3$ units/kg, more preferably $3.3 \times 10^5$ units/kg.

Formulation

The purified IL-2 is rendered aqueous, its concentration is adjusted, if necessary, to 0.01 to 2 mg/ml, and a water-soluble carrier is added to the desired level. The carrier will typically be added such that it is present in the solution at about 1% to 10% by weight, preferably about 5% by weight. The exact amount of carrier added is not critical. Conventional solid bulking agents that are used in pharmaceutical tablet formulation may be used as the carrier. These materials are water soluble, do not react with the IL-2, and are themselves stable. They are also preferably non-sensitive to water (i.e., nonhygroscopic). Specific examples of carriers that may be added include dextrose, lactose, mannitol, sucrose, and other reduced sugars such as sorbitol, starches and starch hydrolysates derived from wheat, corn, rice, and potato, microcrystalline celluloses, and albumin such as human serum albumin. Mannitol, sucrose, and dextrose are preferred.

The carrier adds bulk to the formulation such that when unit dosage amounts of the solution are lyophilized in containers, such as sterile vials, the freeze-dried residue will be clearly discernible to the naked eye. In this regard the preferred carrier, mannitol, yields an aesthetically acceptable (white, crystalline) residue that is not sensitive to water. The nonsensitivity of mannitol to water may enhance the stability of the formulation.

EP publication 215,658, published Mar. 25, 1987, entitled "An Improved Formulation for Lipophilic Proteins" (Hanisch et al.) outlines an improved process for recovering and purifying lipophilic recombinant proteins such as IL-2 from microorganisms to yield a protein preparation which may be formulated into a stable pharmaceutical composition. Such a composition carrying a therapeutically effective amount of the biologically active recombinant lipophilic protein dissolved in a non-toxic, insert, therapeutically compatible aqueous-based carrier medium at a pH of 6.8 to 7.8 also contains a stabilizer for the protein, such as human serum albumin, normal serum albumin and human plasma protein fraction. The formulation aspects of said EP publication 215,658 are herein incorporated by reference as an alternative formulation route for the purified IL-2. EP publication 215,658 outlines a low pH formulation process. U.S. Pat. No. 4,462,940 to Hanisch et al., outlines a high pH formulation process, and the formulation aspects thereof are also herein incorporated by reference.

After adding the carrier, the unit dosage amounts (i.e., for IL-2 volumes that will provide 0.01 to 2 mg, preferably 0.2 to 1.0 mg, IL-2 per dose) of the solution are dispensed into containers, the containers are capped with a slotted stopper, and the contents are lyophilized using conventional freeze-drying conditions and apparatus.

The lyophilized, sterile product consists of a mixture of (1) IL-2, (2) carrier (dextrose, sucrose, or mannitol), (3) optionally other excipients such as human serum albumin, Tween 80, and the like and (4) a small amount of buffer that will provide a physiological pH when the mixture is reconstituted. The product may also contain a minor amount of a preservative to enhance chemical stability. The recombinant IL-2 will typically constitute about 0.015% to 10% by dry weight of the mixture, more preferably about 2% to 5% of the mixture.

The lyophilized mixture may be reconstituted by injecting a conventional parenteral aqueous injection such as distilled water for injection, Ringer's solution injection, Hank's solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml, preferably 1 to 2 ml.

In an alternative formulation, described in U.S. Pat. No. 4,766,106, entitled "Solubilization of Recombinant Proteins for Pharmaceutical Compositions Using Homopolymer Conjugation" to M. Knauf et al., the disclosure of which is incorporated herein by reference, the IL-2 is reacted with an activated polymer selected from polyethylene glycol, homopolymers and polyoxyethylated polyols such as polyoxyethylated glycerol. The polymer preferably has a molecular weight of from 300 to 100,000 daltons, more preferably 350 to 40,000 daltons. The polymer is activated by conjugation with a coupling agent having terminal groups reactive with both the free amine or thiol groups of the protein and the hydroxyl group of the polymer. Examples of such coupling agents include hydroxynitrobenzene sulfonic ester, cyanuric acid chloride, and N-hydroxysuccinimide. The IL-2 is then formulated directly with the water-soluble carrier and buffer as described above, the formulation is lyophilized, and the lyophilized mixture may be reconstituted as described above.

The reconstituted formulation prepared as described above is suitable for parenteral and oral administration to humans or other mammals in therapeutically effective amounts (i.e., amounts which eliminate or reduce the patient's pathological condition) to provide therapy thereto. IL-2 therapy is appropriate for a variety of immunomodulatory indications such as T cell mutagenesis, induction of cytotoxic T cells, augmentation of natural killer cell activity, induction of IFN-γ, restoration and enhancement of cellular immunity (e.g., treatment of immune deficient conditions), and augmentation of cellmediated anti-tumor activity.

Non-ionic surfactants can also be used parenterally as shown in U.S. Ser. No. 101,175. This application discloses a substantially aqueous, stable pharmaceutical composition of matter suitable for parenteral administration comprising a therapeutically effective amount of recombinant IL-2 dissolved in an inert carrier medium comprising as a stabilizer, an effective amount of one or more biocompatible non-ionic polymeric detergents selected from the group consisting essentially of: octylphenoxy polyethoxy ethanol compounds; polyethylene glycol monostearate compounds; and polyoxyethylene sorbitan fatty acid esters. These non-ionic surfactants are useful to stabilize and solubilize IL-2 in an aqueous medium.

The formulations of this invention are useful for parenteral administration, for example, intravenous, subcutaneous, intramuscular, intraorbital, ophthalmic, intracapsular, intraspinal, intrasternal, topical, intranasal aerosol, scarification, and also, for oral administration. The preferred routes of administration are by intramuscular, subcutaneous and intravenous injection, and by topical administration. The use of nonionic detergents is also preferred for topically administered formulations because of their ability to penetrate the skin surface.

Figure 1:
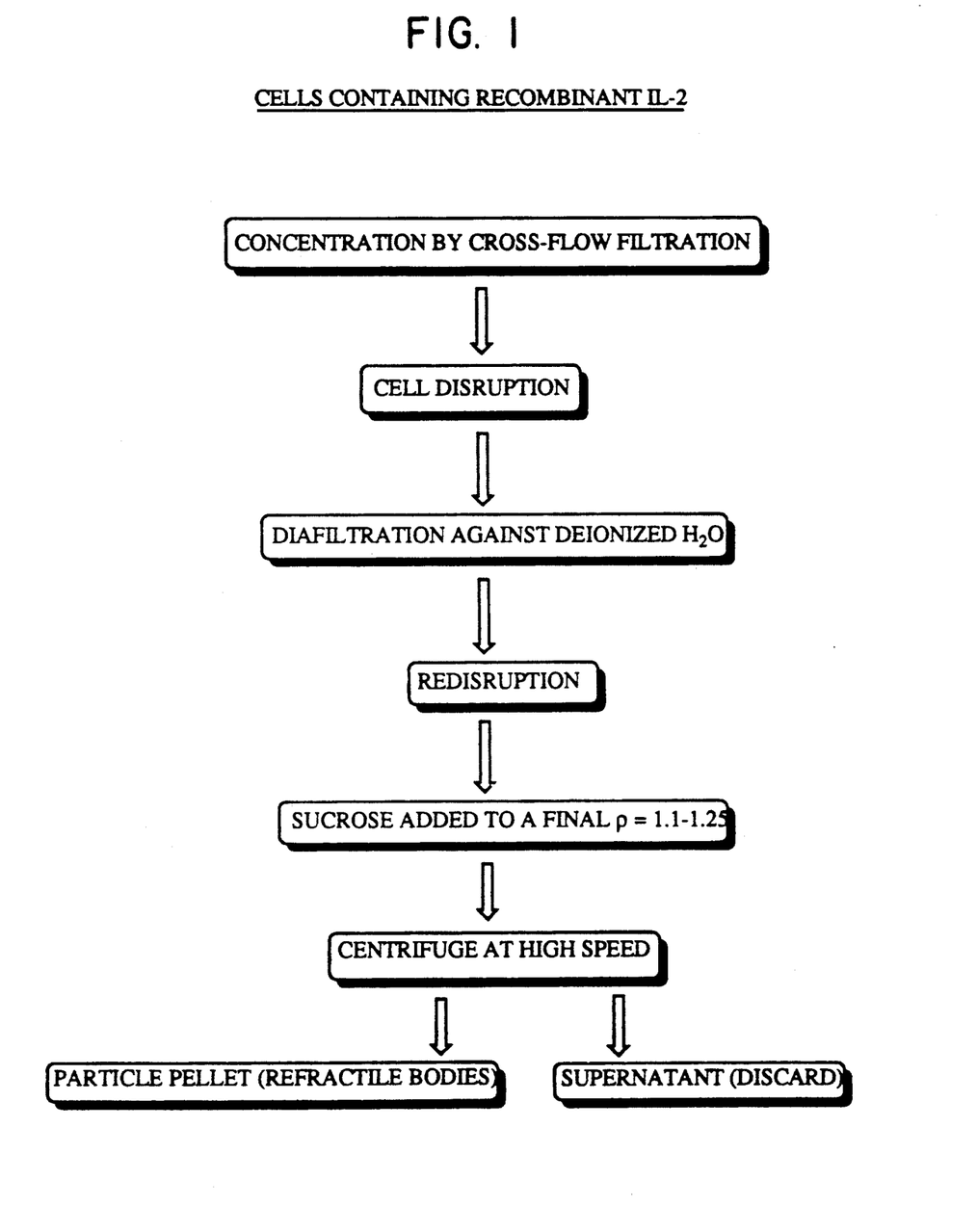
FIGS. 1 and 2 are flow diagrams of the preferred process.
Figure 2:
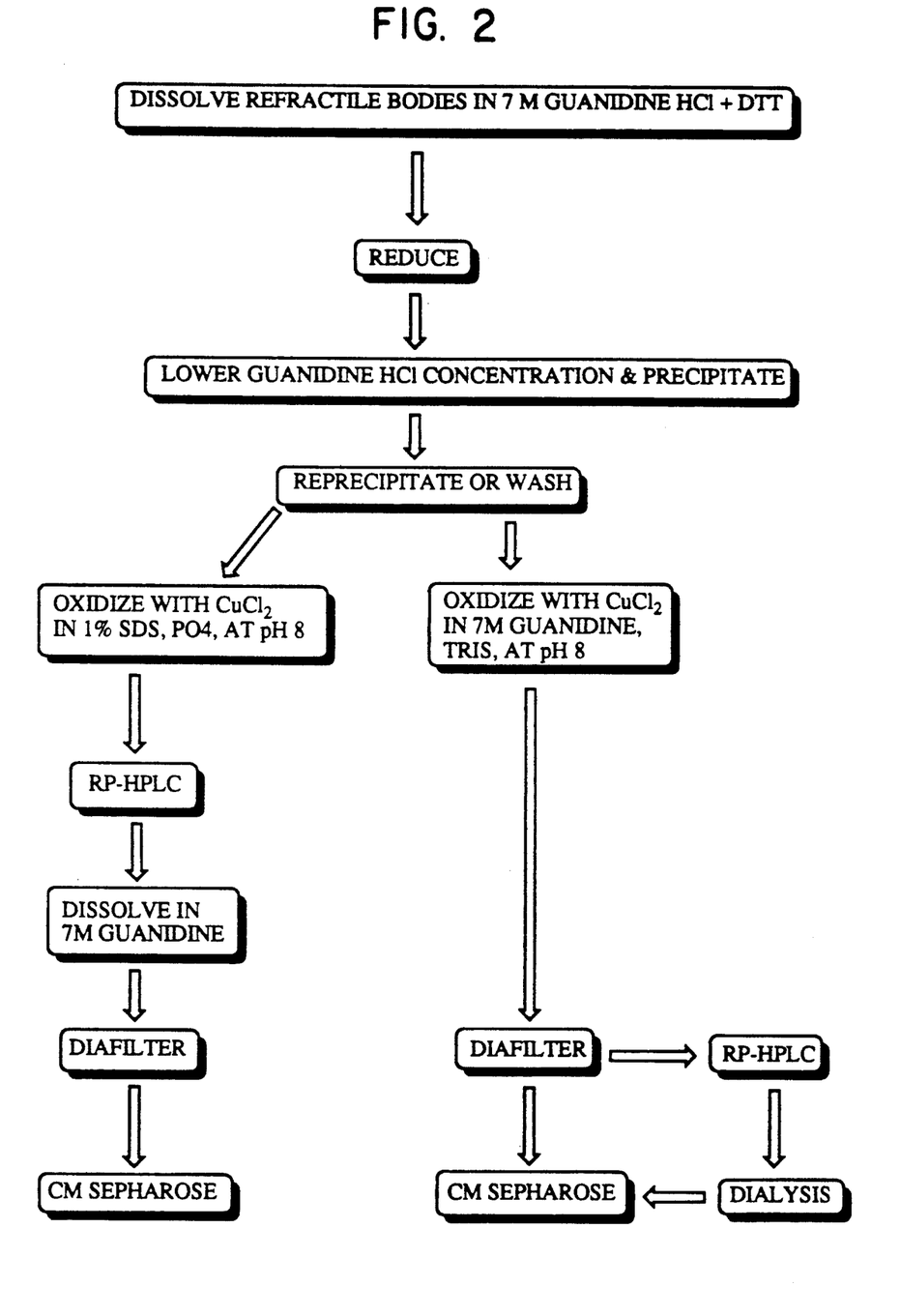

The following examples further illustrate the process and composition of the invention. These examples are not intended to limit the invention in any manner. In these examples all temperatures are in degrees Celsius unless otherwise indicated. FIGS. 1 and 2 indicate the preferred process of this invention, represented by the examples.

EXAMPLE 1

This example illustrates a preferred process for recovering, purifying and formulating recombinant IL-2.

Des-alanyl-IL-$2_{ser}$125 was recovered from *E. coli*. The strain of des-alanyl-IL-$2_{ser}$125-producing *E. coli* (K12/MM294-1) carrying plasmid pLW45 used in this example was deposited at the American Type Culture Collection of Mar. 4, 1984 under accession number 39,626. Said analog and a method of preparation are disclosed in U.S. Pat. No. 4,518,584. The *E. coli* thus transformed with plasmid pLW45 were grown in a 1000-liter fermenter at 37° C. The dissolved oxygen was maintained at about 40% by, as necessary, (1) increasing agitation; (2) adding air; and (3) adding oxygen.

Once the fermenter was filled with water to the operating volume, the following trace elements were added:

| | |
|---|---|
| $ZnSO_4.7H_2O$ | 30 mM |
| $MnSO_4.4H_2O$ | 30 mM |
| $CuSO_4.5H_2O$ | 3 mM |
| $Na_3$ citrate.$2H_2O$ | 1.5 mM |
| $KH_2PO_4$ | 21 mM |
| $(NH_4)_2SO_4$ | 72 mM. |

The fermenter feed and addition vessels were then sterilized according to standard operating procedures. Then the following sterile additions were made:

| | |
|---|---|
| $MgSO_4.7H_2O$ | 3 mM |
| $FeSO_4.7H_2O$ | 72 mM |
| L-tryptophan | 70 mg/L |
| thiamine.HCl | 20 mg/L |
| glucose | 50 g/L |
| tetracycline | 5 mg/L. |

The fermenter was cooled and inoculated with frozen or seed *E. coli* culture at 2 mg/L dry weight cells. Throughout fermentation, the pH is maintained at 6.8 using KOH. Optical density measurements and residual glucose measurements on samples were taken at 14–16 hours and approximately one hour intervals thereafter.

Induction of des-alanyl-IL-$2_{ser}$125 production by depletion of L-tryptophan from the culture medium occurred at about $OD_{680}=10$ followed by the addition of casamino acids to a final concentration of 2% at $OD_{680}=15$. Cultures were harvested about 3–5 hours later. The refractile bodies containing the des-alanyl-IL-2-$ser_{125}$ were then isolated. The harvested material was concentrated about 5–10 fold by circulating the harvest material under pressure through UF cross-flow filtration cartridges with a 100K molecular weight cutoff. The cells were disrupted by 3 passes through a disrupter at about 6500 psi (195 atm).

EDTA was then added to a final concentration of 5 mM. The suspension was diafiltered against 5 volumes of deionized water. Octanol was added to 1% (v/w) to kill any residual live bacteria in the diafiltered product. Two mM EDTA was added and after several hours, the diafiltered disruptate was redisrupted by passing it through a disrupter.

Sucrose was added to the redisruptate to create a final density between 1.1 and 1.25 g/ml. The mixture was centrifuged at 8,000 to 20,000×g at 1–2 lpm, and the particle pellet or paste was collected. A temperature of at least 20° C. was maintained prior to and during centrifugation.

The particle paste was then mixed with 17 ml per gram of paste of an aqueous solution of saturated guanidine hydrochloride, DTT, 50 mM, Tris, 50 mM, and 25 mM EDTA, the pH was adjusted to 8.0 with NaOH and heated to 40° C. for about 10 minutes. Undissolved materials were removed from the mixture by centrifugation at 3000×g for 15 minutes.

The next step in the purification was to remove the DTT and EDTA from the IL-2 solution (supernatant) by gel filtration using a Sephadex~G-25 column. The column was run in 7M guanidine hydrochloride buffer at pH 7.5. Using a process chromatogram, the IL-2 peak was collected and the peak was diluted with guanidine hydrochloride buffer to a protein concentration of 0.5 mg/ml.

Oxidation of the IL-2 was initiated by adding $CuCl_2$ in a molar ratio of 3:1 ($CuCl_2$ to IL-2). The oxidation was carried out at about 25° C. in 7M guanidine hydrochloride, 10 mM phosphate. The pH was controlled at 7.5±0.2 during oxidation and 4 mM EDTA was added when the oxidation was completed. Since oxidized IL-2 is more hydrophilic than reduced IL-2, the progress of the oxidation reaction was monitored by RP-HPLC.

The resulting solution of oxidized IL-2 was then diluted with 10 mM phosphate buffer to reduce the guanidine hydrochloride concentration to 2M. The IL-2 concentration was then increased to 2.5 mg/ml using a hollow fiber membrane ultrafiltration unit with a 10,000 dalton cutoff. The solution was then further diluted with 10 mM phosphate buffer to 0.2M guanidine hydrochloride and allowed to sit overnight at 4° C. to obtain a precipitate.

The precipitate consisting of extraneous *E. coli* proteins and some IL-2 was then removed by filtering with a cellulose acetate filter to obtain approximately 85% recovery of refolded IL-2. $(NH_4)_2SO_4$ was then added to the supernatant to a concentration of 1.25M. This solution was loaded onto a Pharmacia Phenyl Fast-Flow Sepharose hydrophobic interaction column. IL-2 was recovered from the column with a decreasing $(NH_4)_2SO_4$ gradient with the IL-2 collected in the fractions at about 0.95 to 0.75M $(NH_4)_2SO_4$. The pooled fractions were diafiltered and then loaded on a Pharmacia carboxymethyl (CM) Fast-Flow Sepharose ion exchange column at pH 7 equilibrated with 10 mM phosphate buffer. IL-2 fractions were recovered at about 0.15M NaCl.

The resulting IL-2 was 98% pure by SDS-PAGE analysis and homogeneous by HPLC analysis. Its specific activity was $8 \times 10^6$ units/mg as measured by the HT-2 cell proliferation assay. Enzyme-linked immunosorbent assays (ELISA) were carried out to determine whether this renatured recombinant IL-2 (guanidine-process IL-2) binds to polyclonal antibodies that bind to the recombinant IL-2 made by the process described in U.S. Pat. No. 4,569,790, which process is incorporated herein by reference, in which the IL-2 is solubilized with SDS (SDS-process IL-2). Serum from a patient treated with SDS-process IL-2 was diluted 1:1000 in assay buffer (PBS with 0.5% BSA and 0.05% Tween 20) and mixed with SDS or guanidine-process IL-2 in final concentrations of 0 to 5 mg/ml. After a two hour room temperature incubation, the mixtures were applied in 100 ml volumes to 96 well microelisa plates (Immulon I, Dynatech) previously coated with SDS-process IL-2 (5 mg/ml in 0.05M Na$_2$CO$_3$, pH 9.6, 100 ml/well). The mixtures were allowed to sit in the IL-2-coated wells for thirty minutes, at which time the plates were thoroughly washed in PBS with 0.05% Tween 20, and peroxidase-conjugated goat anti-human IgG (Cappel, 1:1000 dilution) was added. After another two hour incubation the second antibody was removed and substrate added (OPD, Sigma, 100 ml/well). The enzymatic reaction was quenched twenty minutes later by the addition of 50 ml 2N HCl to each well. Absorbances at 490 nm were measured using a Dynatech MR580 plate reader (reference wavelength 405 nm). The results showed that guanidine-process IL-2 did not compete significantly.

EXAMPLE 2

Example 1 was repeated through the IL-2 refolding step (recovery of supernatant following reduction of guanidine hydrochloride to 0.2M).

The IL-2 solution (8.8 mg of protein) was acidified with trifluoroacetic acid to a pH of 2.1 and then centrifuged to remove any precipitate. This was loaded on a 1.25 cm by 30 cm column of Vydac C-4 silica equilibrated with 0.1% trifluoroacetic acid in water. The column was eluted with a gradient of acetonitrile containing 0.1% trifluoroacetic acid. The fractions of pure IL-2 were pooled and then dialyzed into 7M guanidine pH 7.5 buffer. This was then dialyzed against 10 mM phosphate buffer pH 7.0. A precipitate was removed by microcentrifugation to recover 68% of the IL-2 in the supernatant.

EXAMPLE 3

Example 1 was repeated through the recovery of the refractile body particle paste.

About 113.7 g of solid guanidine (7M final concentration) was added to 14 g of the particle paste followed by addition of 10 mM Tris/2 mM EDTA buffer to about 190 ml. After homogenizing, 1.5 g of solid DTT (50 mM final concentration) was added and the pH was adjusted to 8–8.5 with NaOH. The solution was warmed to 50° C. for 15 minutes to promote reduction. The solution was then diluted with 10 mM Tris/2 mM EDTA to a final volume of 200 ml.

The next step in the purification was to remove the reducing agent and other contaminants from the IL-2 material. About 25 ml of the reduced IL-2 were diluted to approximately 5–10 mg IL-2/ml with 75 ml 7.0M guanidine. This solution was diluted to 4.8M guanidine with Tris/EDTA buffer and allowed to stand two hours. Very little precipitate was formed, and the precipitate was removed by centrifugation at 10,000×g for 15 minutes. The supernatant was diluted to 4.0M guanidine with Tris/EDTA buffer and allowed to stand two hours at room temperature. The heavy precipitate was collected by centrifugation (10,000 g×15 minutes).

The pellet was washed once with 50 ml 2% Tween 80 and twice with 50 ml H$_2$O. 16.7 g of solid guanidine was added and the solution was brought to 25 ml with water. The solubilized IL-2 was diluted to 1 mg/ml with 7.0M guanidine in 10 mM Citrate, pH 6.5. CuCl$_2$ (to 0.1 mM) was added and the pH was adjusted to 8–8.5. This solution was allowed to stir overnight.

Using a YM spiral-wound cartridge, the guanidine was diafiltered away and the IL-2 was concentrated to about 2 mg/ml. Care was taken to remove air from the system because soluble IL-2 is sensitive to agitation, especially with air bubbles. It was diafiltered against 10 volumes of 2.5% sucrose and 140 mM NaCl in 10 mM NaCitrate pH 6.5 solution. After centrifugation at 3000 g×15 minutes, 600 ml of supernatant containing 0.63 mg/ml of IL-2 was collected. The ionic strength was reduced by dialysis into 10 mM NaCitrate, pH 6.5 before proceeding.

The chromatography consisted of two columns, each equilibrated with 10 mM NaCitrate pH 6.5 buffer. The first column was packed with DEAE Sepharose Fast Flow (Pharmacia). 25 ml of 0.63 mg IL-2/ml in 10 mM NaCitrate pH 6.5 was run through a 1×10 cm column at 0.5 ml/minute. The NaCl concentration of the pool was adjusted to 40 mM NaCl. The second column was packed with CM Sepharose Fast Flow (Pharmacia). 28.5 ml of 0.38 mg IL-2/ml was loaded at 0.5 ml/min. The IL-2 bound to the gel and was eluted with an increasing NaCl gradient (40–400 mM NaCl in 10 mM NaCitrate pH 6.5, 0.3 ml/min) over 6 hours. About 12.6 ml of 0.71 mg of IL-2 per ml was pooled.

The CM pool was desalted into 10 mM sodium citrate pH 6.5 over G25 Sephadex to remove NaCl and provide a well characterized buffer for formulation.

The resulting IL-2 was over 99% pure by analytical RP-HPLC.

EXAMPLE 4

About 5 ml of IL-2-containing refractile bodies, slurred with an equal volume of water was dissolved with guanidine buffer. The solution had a guanidine concentration of 7M and a volume of 35 ml. The pH of the solution was adjusted to about 8.0 with 3M Tris base. Next, 0.3 g of DTT was added and the solution was heated to about 45° C. for 15 minutes. The solution was then diluted with an equal volume of 0.1M citrate pH 5.0 buffer and allowed to stand for 1.5 hours. The formed precipitate was separated by centrifugation (10,000×g for 10–20 minutes). The precipitate was washed four times with 70 ml of 3.5M guanidine and twice with 70 ml of water. The precipitate was dissolved in 7M guanidine and was analyzed by RP-HPLC. Approximately 265 mg of IL-2 were recovered in about 90% purity.

EXAMPLE 5

IL-2 was produced from cells and refractile bodies obtained in a manner similar to the above examples. They were purified using a guanidine-renaturation purification with, and without, RP-HPLC.

2.5 to 3.3 gm of IL-2 in 40–60 ml of refractile body slurry was purified using the guanidine-renaturation purification followed by ion exchange chromatography. In the first run, a RP-HPLC was included before the renaturation step to remove IL-2 having oxidized methionine residues and *E. coli* impurities. In the second run, the HPLC step was omitted.

1. Purification with RP-HPLC in the process: A solution was made containing: 60 ml of refractile body slurry, 121 gm of guanidine-HCl, 0.6 gm of DTT, 3.6 ml of 0.25M EDTA pH 8.0 and 24 ml of water to a final volume of 180 ml (20 mM DTT, 5 mM EDTA, and 7M guanidine). The pH of the solution was adjusted to 8.5 with NaOH and the IL-2 was reduced at 30° C. for 20 minutes. The solution was centrifuged to remove the undissolved material and the pH was adjusted to 5.0 with HoAc. The reduced IL-2 was precipitated by lowering the guanidine concentration to 3.5M by adding an equal volume of a buffer solution containing: 20 mM DTT, 5 mM EDTA, 10 mM NaOAc, at pH 5.0.

After 15 minutes to one hour at room temperature, the precipitate was centrifuged at 10,000 rpm for 10 minutes to obtain an IL-2 pellet. The IL-2 pellet was then washed 2 times with 200 ml of a buffer solution containing 3.5M guanidine, 10 mM NaOAc, at pH 5.0 and 3 times with 200 ml of a buffer solution containing 10 mM NaOAc at pH 5.0 to remove DTT, E. coli impurities, and guanidine. The pellet was redissolved in 160 ml of 5% SDS and 50 mM NaPO$_4$ at pH 8.0. The protein and SDS concentrations were adjusted to 1 mg/ml and 1% respectively with 50 mM NaPO$_4$ at pH 8.0 and then oxidized with 0.2 mM CuCl$_2$ overnight at room temperature. The next morning, 300 ml of HoAc was added to the 2500 ml of oxidized material to a final concentration of 12% HoAc and 1971 ml was loaded onto a Vydac C-4 RP-HPLC (5×50 cm). The HPLC was run and fractions, which contained a low concentration of oxidized methionine residues as determined by an analytical RP-HPLC, were pooled. The pool (375 ml) was then precipitated by adding an equal volume of 0.8N NaOH and then the precipitate was centrifuged at 10,000 rpm for 30 minutes. The HPLC pellet was redissolved in a buffer solution (956 ml of 7M guanidine, 10 mM Na citrate, at pH 6.5) to contain 1 mg/ml IL-2. The solution was diafiltered (against 2.5% sucrose, 40 mM NaCl, 10 mM Na citrate, pH 6.5 buffer) with an Amicon YM-10 cartridge to remove guanidine from the solution. After 10 volume changes with a citrate buffer, the retentate (1180 ml) was filtered with a Nalgene cellulose acetate membrane to obtain a CM Sepharose loading material. About 11% of the filtered retentate (129 ml) was further purified with CM Sepharose fast flow.

2. Purification without the HPLC in the process: 42 ml of IL-2 refractile body slurry was reduced with DTT and precipitated by lowering the guanidine concentration to 3.5M as described above. The pellet was then washed 3 times with 200 ml of a buffer containing 3.5M guanidine, 10 mM NaOAc, at pH 5.0. The washed pellet was redissolved in a buffer containing 2500 ml of 7M guanidine, 10 mM Tris, at pH 8.0 to 1 mg/ml of IL-2 and oxidized with 0.2 mM CuCl$_2$ overnight at room temperature. EDTA was added to 2 mM final concentration before diafiltration with a solution containing 2.5% sucrose, 40 mM NaCl, 10 mM Na citrate, at pH 6.5 (using a YM-10 cartridge for 10 volume changes). About 7% of the filtered retentate (45 ml) was further purified by CM Sepharose fast flow.

Using either purification method, final purified materials were obtained which had no detectable amount of E. coli antigen by the ELISA assay (less than 25 ng/mg of IL2). The western blots of goat anti-IL-2 E. coli of the CM pools also support the results from the ELISA. The process which does not have the RP-HPLC step produced the final material with higher % of IL-2 having oxidized methionine residues (4.4%) than from the process with the HPLC (1.7%). Thus the RP-HPLC is not necessary to obtain a high purity IL-2 with no detectable amount of E. coli antigen, but is necessary to obtain a lower percentage of IL-2 with oxidized methionine residues in the final product.

EXAMPLE 6

Reduced IL-2 is very soluble in 7M guanidine and only slightly soluble in a guanidine solution less than 4M. This differential solubility can be exploited to partially purify IL-2. If IL-2 containing refractile bodies are dissolved in 7M guanidine with DTT and diluted to reduce the guanidine concentration to 3.5M, the partially purified IL-2 is recovered as a precipitate. The precipitate can then be washed with 3.5M guanidine to remove any adherent supernatant. Experiments were conducted to see if redissolving and reprecipitating the partially purified IL-2 precipitate would be more effective than simply washing the precipitate in 3.5M guanidine.

Twelve ml of a slurry of refractile bodies in water (1/1) were mixed with 25 g of guanidine, 0.6 ml 0.25M EDTA pH 8.0, 0.12 g DTT, 2 ml 1.5M tris HCl pH 8.8 and 1.5 ml water. The solution was stirred for 1.5 hours and then centrifuged for 10 min at 10,000×g. 33.5 ml of supernatant was obtained. 33 ml of the supernatant was mixed with 33 ml of 0.1M Na citrate pH 5.0. After about 2 minutes the mixture was equally divided into two centrifuge tubes and spun at 10,000×g for 15 minutes. The precipitate from one of the tubes was washed with 3.5M guanidine, 0.1M acetate pH 5.0 buffer and recentrifuged, twice. The precipitate from the other tube was dissolved in 17 ml of 7M guanidine (final concentration) pH 5.0 citrate buffer and the IL-2 was precipitated out by adding 17 ml of water. Following centrifugation, the dissolution, precipitation and centrifugation was repeated. The reduced refractile bodies, the washed pellet and the reprecipitated pellet were dissolved in 7M guanidine and compared by RP-HPLC.

The purities of the refractile bodies, washed pellet and the reprecipitated pellet are in the following table. The yield of reduced IL-2 from refractile bodies was about 80% in both cases. The greater purity obtained by repeated dissolving and precipitation indicates that some soluble impurities are partially coprecipitated with the reduced IL-2. These partially coprecipitated impurities are more effectively removed by repeating the dissolving and precipitation cycle than by simply washing the refractile bodies with 3.5M guanidine.

| Sample | % IL-2 Purity |
|---|---|
| Refractile Bodies | 44% |
| Washed Precipitate | 51% |
| Redissolved and Reprecipitated Precipitate | 63% |

EXAMPLE 7

IL-2 was prepared in a similar manner to that shown in Example 5 (IL-2 purification without RP-HPLC). The following steps were performed after oxidation with CuCl$_2$ in 7M guanidine (oxidized at 0.5 mg/mL protein and 100 µM CuCl$_2$). One liter of IL-2 containing material was prepared and diafiltered against 1M guanidine, 10 mM Na citrate, 40 mM NaCl, 2.5% sucrose, pH 6.5. After 3 volume exchanges, the material was recovered and filtered through a 0.2 µM filter. Then the material was diafiltered against 0.5M guanidine with the same other species. After 3 volume changes, the material was again recovered and filtered as before. The material was returned to the diafiltration setup and diafiltration was continued against 3 volumes changes of 10 mM Na citrate, 40 mM NaCl, 2.5% sucrose, pH 6.5. The recovered material was filtered through a 0.2 µM filter.

The diafiltered IL-2, prepared above, was run on preparative HPLC under simulated production conditions. Afterwards, the IL-2 containing material was dialyzed to remove the HPLC solvents. It was done in two stages; i.e., dialysis into standard dialysis buffer at pH 2.7 followed by dialysis into standard dialysis buffer at pH 7.

From the foregoing it may be seen that the present process provides advantages as regards: (1) simplicity of the purification process, (2) the absence of solubilizing agent in the final product, and (3) recombinant IL-2 product that appears to be less immunogenic than that previously made.

In addition to the aforedescribed vector system employing the trp promoter for IL-2 expression, alternative vector systems include the use of the lambda pL promoter and/or a positive retroregulatory element. These vector systems are described in U.S. Pat. Nos. 4,711,845, issued Dec. 8, 1987, and 4,666,848, issued May 19, 1987, the disclosures of both are incorporated herein by reference.

Vector systems described in the aforedescribed patents, as well as additional vectors provided below, have been deposited with the American Type Culture Collection (ATCC), 12301 Parklawn Drive, Rockville, Md. under the terms of the Budapest Treaty on the International Recognition of the Deposit of Micro organisms for the Purpose of Patent Procedure and Regulations thereunder and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers:

| Plasmid | ATCC No. | Deposit Date |
|---|---|---|
| pFC54 in E. coli DG95 lambda (N$_7$N$_5$3cI857SusP$_8$0) | 39831 | 4 September 1984 |
| pFC54.t in E. coli DG95 lambda | 39789 | 31 July 1984 |
| pHCW701 in E. coli K12 MM294 | 39757 | 8 June 1984 |
| pLW1 in E. coli K12 MM294 | 39405 | 25 July 1983 |
| pLW46 in E. coli K12 MM294 | 39452 | 29 September 1983 |
| pLW55 in E. coli K12 MM294.1 | 39516 | 29 September 1983 |
| pSY3001 in E. coli K12 MM294 | 39949 | 19 December 1984 |

Modifications of the above-described modes for carrying out the invention which are obvious to those of skill in the fields of biochemistry and related fields are intended to be within the scope of the following claims.

We claim:

1. A process for purifying recombinant IL-2 from a transformed microorganism containing the IL-2, comprising:
    (a) isolating water insoluble IL-2 containing material;
    (b) dissolving the water insoluble IL-2 containing material in a sufficient amount of a guanidine salt and a reducing agent;
    (c) reducing the concentration of the guanidine salt, so that the IL-2 precipitates and the soluble proteins from the transformed microorganism are removed
    (d) redissolving the IL-2 precipitate in a sufficient amount of a guanidine salt;
    (e) oxidizing the IL-2 to form the natural disulfide bridge in IL-2;
    (f) reducing the guanidine concentration to precipitate insoluble proteins from the transformed microorganism while IL-2 remains substantially soluble; and
    (g) separating and removing the insoluble proteins from the soluble IL-2.

2. A process in accordance with claim 1 further comprising washing the IL-2 precipitate of step (c) in acetate or a guanidine solution having a concentration between 2 and 4M.

3. A process in accordance with claim 1 further comprising: (h) lowering the guanidine concentration to below 0.5M by diafiltration; and (i) purifying the IL-2 by CM Sepharose chromatography.

4. A process in accordance with claim 1 further comprising: (h) lowering the guanidine concentration to below 0.5M by diafiltration; (i) purifying the IL-2 by reverse phase HPLC; (j) dialyzing the resulting IL-2 solution; and (k) purifying the IL-2 by CM Sepharose chromatography.

5. The process as recited in claim 4 further comprising adding a stabilizer to the solution to prevent aggregation during diafiltration.

6. The process as recited in claim 5 wherein the stabilizer is selected from the group consisting essentially of arginine and glycine.

7. The process of claim 1 wherein the IL-2 is des-ala-IL-2$_{ser}$125.

8. The process of claim 1 wherein the IL-2 composition is substantially free of pyrogens as determined by the U.S.P. rabbit pyrogen test at a dosage of $1.0 \times 10^3$ units per kg.

9. The process of claim 1 wherein the IL-2 composition is substantially free of pyrogens as determined by the U.S.P. rabbit pyrogen test at a dosage of $3.3 \times 10^5$ units per kg.

10. A process for recovering purified renatured recombinant IL-2 from a transformed microorganism containing the IL-2 comprising:
    (a) disrupting the cell membrane and cell wall of the microorganism;
    (b) separating water insoluble IL-2 containing material from the disruptate;
    (c) mixing the insoluble IL-2 containing material of step (b) at a pH of about 7 to about 9 with an aqueous solution of a reducing agent and a guanidine salt whereby the IL-2 in the insoluble material is dissolved and denatured;
    (d) precipitating the IL-2 out of the IL-2-containing solution and recovering the precipitate;
    (e) solubilizing the IL-2 precipitate in a chaotropic agent;
    (f) oxidizing the IL-2 in the solution while maintaining the concentration of chaotropic agent at a strongly denaturing concentration, whereby the natural disulfide bridge of IL-2 is formed;
    (g) purifying the oxidized IL-2 in the supernatant by (1) reverse-phase high performance liquid chromatography followed by dissolution of the pool in a solution of chaotropic agent and removal of the chaotropic agent from the solution, or (2) hydrophobic interaction chromatography combined with ion exchange chromatography, or (3) ion exchange chromatography;
    (h) reducing the concentration of chaotropic agent in the solution to a level at which the oxidized IL-2 is permitted to renaturate and a precipitate forms;
    (i) separating the precipitate of step (h) from the solution to provide a supernatant; and (j) recovering a purified oxidized, soluble heterologous human IL-2 composition having an IL-2 content of at least about 95% as determined by reducing sodium dodecyl sulfate polyacrylamide gel electrophoresis analysis, a solubility in phosphate buffered saline of at least about 5 mg IL-2 per ml, a specific activity of at least about $1 \times 10^7$ units/mg as determined by HT-2 cell proliferation assay, and an endotoxin content of less than about 0.1 nanograms per mg of IL-2.

11. The process of claim 10 wherein the chaotropic agent of step (e) is guanidine hydrochloride and the strongly denaturing concentration is at least about 6M.

12. The process of claim 11 wherein the chaotropic agent is guanidine hydrochloride and the strongly denaturing concentration is in the range of 6 to 9M.

13. The process of claim 11 wherein the reducing agent is dithiothreitol.

14. The process of claim 10 wherein in step (d) the IL-2 precipitate is formed by reducing the guanidine salt concentration to below about 5M.

15. The process of claim 14 wherein the guanidine salt concentration is about 3 to 4M.

16. The process of claim 14 wherein the IL-2 precipitate is collected by centrifugation and is washed prior to step (d).

17. The process of claim 14 wherein the IL-2 is redissolved with a guanidine salt and is reprecipitated by diluting the guanidine salt prior to step (e).

18. The process of claim 16 wherein the IL-2 is washed with 2-4M guanidine hydrochloride.

19. The process of claim 16 wherein the IL-2 is washed with 1-2% of a polysorbate 80 compound.

20. The process of claim 10 wherein the oxidation is a controlled oxidation using $Cu^{+2}$ ion as an oxidation promoter or o-iodosobenzoic acid as an oxidizing agent.

21. The process of claim 11 wherein in step (h) the concentration of guanidine hydrochloride is reduced to below about 2M.

22. The process of claim 21 wherein in step (h) the concentration of guanidine hydrochloride is reduced to below about 0.5M.

23. The process of claim 12 wherein: the reducing agent is dithiothreitol; the IL-2 in step (d) is precipitated by the reducing the concentration of guanidine hydrochloride to below 5M; the oxidation is a controlled oxidation using $Cu^{+2}$ ion as an oxidation promoter; the concentration of guanidine hydrochloride in step (h) is reduced to below 0.5M; and the oxidized IL-2 in the supernatant is purified by reverse-phase high performance liquid chromatography in step (g).

24. The process of claim 23 wherein the IL-2 is des-ala-IL-$2_{ser}125$.

25. A process for recovering purified renatured recombinant IL-2 from a transformed microorganism containing the IL-2 comprising:
(a) disrupting the cell membrane and cell wall of the microorganism;
(b) separating water insoluble IL-2 containing material from the disruptate;
(c) mixing the insoluble IL-2 containing material of step (b) at a pH of about 7 to about 9 with an aqueous solution of a reducing agent and a guanidine salt whereby the IL-2 in the insoluble material is dissolved and denatured;
(d) precipitating the IL-2 out of the IL-2-containing solution and recovering the precipitate;
(e) solubilizing the IL-2 precipitate in a chaotropic agent;
(f) oxidizing the IL-2 in the solution while maintaining the concentration of chaotropic agent at a strongly denaturing concentration, whereby the natural disulfide bridge of IL-2 is formed;
(g) reducing the concentration of chaotropic agent in the solution to a level at which the oxidized IL-2 is permitted to renaturate and a precipitate forms;
(h) separating the precipitate of step (g) from the solution to provide a supernatant;
(i) purifying the oxidized IL-2 in the supernatant by (1) reverse-phase high performance liquid chromatography followed by dissolution of the pool in a solution of chaotropic agent and removal of the chaotropic agent from the solution, or (2) hydrophobic interaction chromatography combined with ion exchange chromatography, or (3) ion exchange chromatography; and
(j) recovering a purified oxidized, soluble heterologous human IL-2 composition having an IL-2 content of at least about 95% as determined by reducing sodium dodecyl sulfate polyacrylamide gel electrophoresis analysis, a solubility in phosphate buffered saline of at least about 5 mg IL-2 per ml, a specific activity of at least about $1 \times 10^7$ units/mg as determined by HT-2 cell proliferation assay, and an endotoxin content of less than about 0.1 nanograms per mg of IL-2.

26. The process of claim 25, wherein the chaotropic agent is guanidine hydrochloride and the strongly denaturing concentration of step (e) is at least about 6M.

27. The process of claim 25, wherein the chaotropic agent is guanidine hydrochloride and the strongly denaturing concentration of step (e) is in the range of 6 to 9M.

28. The process of claim 26, wherein the reducing agent is dithiothreitol.

29. The process of claim 25, wherein in step (d) the IL-2 precipitate is formed by reducing the guanidine hydrochloride concentration to below about 5M.

30. The process of claim 29, wherein the guanidine hydrochloride concentration is about 3 to 4M.

31. The process of claim 29, wherein the IL-2 precipitate is collected by centrifugation and is washed prior to step (d).

32. The process of claim 29, wherein the IL-2 is redissolved with a guanidine salt and is reprecipitated by diluting the guanidine salt prior to step (e).

33. The process of claim 31, wherein the IL-2 is washed with 2-4M guanidine hydrochloride.

34. The process of claim 31, wherein the IL-2 is washed with 1-2% of a polysorbate 80 compound.

35. The process of claim 25, wherein the oxidation is a controlled oxidation using $Cu^{+2}$ ion as an oxidation promoter or o-iodosobenzoic acid as an oxidizing agent.

36. The process of claim 26, wherein in step (g) the concentration of guanidine hydrochloride is reduced to below about 2M.

37. The process of claim 36, wherein in step (g) the concentration of guanidine hydrochloride is reduced to below about 0.5M.

38. The process of claim 27, wherein the reducing agent is dithiothreitol; in step (d) IL-2 is precipitated by reducing the concentration of guanidine hydrochloride to below 5M; the oxidation is a controlled oxidation using $Cu^{+2}$ ion as an oxidation promoter; in step (g) the concentration of guanidine hydrochloride is reduced to below 0.5M; and in step (i) the oxidized IL-2 in the supernatant is purified by ion exchange chromatography.

* * * * *